United States Patent
Wang et al.

(10) Patent No.: US 10,443,059 B2
(45) Date of Patent: Oct. 15, 2019

(54) PHARMACEUTICAL COMPOSITION AND METHOD FOR REDUCING SCAR FORMATION

(71) Applicants: Yi-Wen Wang, Taipei (TW); Niann-Tzyy Dai, Taipei (TW)

(72) Inventors: Yi-Wen Wang, Taipei (TW); Niann-Tzyy Dai, Taipei (TW)

(73) Assignee: Niann-Tzyy Dai, Taipei (TW)

( * ) Notice: Subject to any disclaimer, the term of this patent is extended or adjusted under 35 U.S.C. 154(b) by 351 days.

(21) Appl. No.: 15/124,030

(22) PCT Filed: Mar. 11, 2014

(86) PCT No.: PCT/CN2014/073228
§ 371 (c)(1),
(2) Date: Sep. 7, 2016

(87) PCT Pub. No.: WO2015/135138
PCT Pub. Date: Sep. 17, 2015

(65) Prior Publication Data
US 2017/0016005 A1   Jan. 19, 2017

(51) Int. Cl.
| | | |
|---|---|---|
| *C12N 15/113* | (2010.01) | |
| *A61K 31/713* | (2006.01) | |
| *A61K 38/02* | (2006.01) | |
| *C12N 7/00* | (2006.01) | |
| *A61K 31/7088* | (2006.01) | |
| *A61K 31/7105* | (2006.01) | |

(52) U.S. Cl.
CPC ...... *C12N 15/1138* (2013.01); *A61K 31/7088* (2013.01); *A61K 31/713* (2013.01); *A61K 31/7105* (2013.01); *A61K 38/02* (2013.01); *C12N 7/00* (2013.01); *C12N 2310/14* (2013.01); *C12N 2320/30* (2013.01); *C12N 2740/15041* (2013.01); *C12N 2750/14141* (2013.01)

(58) Field of Classification Search
CPC .. C12N 15/1138; A61K 38/02; A61K 31/713; A61K 31/7088; A61K 31/7105
See application file for complete search history.

(56) References Cited

PUBLICATIONS

Wang et al.; siRNA-Targeting Transforming Growth Factor-Beta Type I Receptor Reduces Wound Scarring and Extracellular Matrix Deposition of Scar Tissue; Journal of Investigative Dermatology; vol. 134, pp. 2016-2025, published online Mar. 27, 2014 (Year: 2014).*
Leung et al.; RNA interference: from gene silencing to gene-specific therapeutics; Pharmacology & Therapeutics, vol. 107, pp. 222-239 (2005) (Year: 2005).*
Lambeth et al.; Short Hairpin RNA-Mediated Gene Silencing; siRNA Design; Methods and Protocols, Methods in Molecular Biology, Chapter 12, vol. 942, pp. 205-232, (2013) (Year: 2013).*
Das et al.; Mechanism of RNA interference (RNAi): Current Concept; 2011 International Conference on Food Engineering and Biotechnology, IPCBEE, vol. 9, pp. 240-245 (2011) (Year: 2011).*
Homo sapiens transfoming growth factor, beta receptor 1 (TGFBR1), transcript variant 1, mRNA, NCBI Reference Sequence: NM_004612. 2, pp. 1-7, available Mar. 15, 2015 (Year: 2015).*

* cited by examiner

Primary Examiner — Antonio Galisteo Gonzalez (57) ABSTRACT

Disclosed herein is a pharmaceutical composition for reducing scar formation in a subject in need thereof. The pharmaceutical composition includes a mixture of three nucleic acids and a pharmaceutically acceptable carrier. A method for reducing scar formation in a subject in need thereof is also disclosed herein.

18 Claims, 7 Drawing Sheets
Specification includes a Sequence Listing.

Scrambled siRNA siTGFBRI-mix

SEQUENCE LISTING

<160> NUMBER OF SEQ ID NOS: 13

<210> SEQ ID NO 1
<211> LENGTH: 25
<212> TYPE: RNA
<213> ORGANISM: Homo sapiens
<220> FEATURE:
<223> OTHER INFORMATION: TGFBRI siRNA-a

<400> SEQUENCE: 1
gacaucuaug caaugggcuu aguau                                    25

<210> SEQ ID NO 2
<211> LENGTH: 25
<212> TYPE: RNA
<213> ORGANISM: Homo sapiens

<400> SEQUENCE: 2
gcaucucacu cauguugaug gucua                                    25

<210> SEQ ID NO 3
<211> LENGTH: 25
<212> TYPE: RNA
<213> ORGANISM: Homo sapiens

<400> SEQUENCE: 3
aguaagacau gauucagcca cagau                                    25

<210> SEQ ID NO 4
<211> LENGTH: 21
<212> TYPE: DNA
<213> ORGANISM: Homo sapiens

<400> SEQUENCE: 4
tgctgctggt caacctggtg c                                        21

<210> SEQ ID NO 5
<211> LENGTH: 20
<212> TYPE: DNA
<213> ORGANISM: Homo sapiens

<400> SEQUENCE: 5
acttccagca ggaccggggg                                          20

<210> SEQ ID NO 6
<211> LENGTH: 20
<212> TYPE: DNA
<213> ORGANISM: Homo sapiens

<400> SEQUENCE: 6
ctggtggtaa aggcgaaatg                                          20

<210> SEQ ID NO 7
<211> LENGTH: 19
<212> TYPE: DNA
<213> ORGANISM: Homo sapiens

<400> SEQUENCE: 7
ccaggagcac cattagcac                                           19

<210> SEQ ID NO 8
<211> LENGTH: 22
<212> TYPE: DNA
<213> ORGANISM: Homo sapiens

-continued

```
<400> SEQUENCE: 8
acaacaccga ggtgactgag ac                                              22

<210> SEQ ID NO 9
<211> LENGTH: 22
<212> TYPE: DNA
<213> ORGANISM: Homo sapiens

<400> SEQUENCE: 9
ggacacaacg atgcttcctg ag                                              22

<210> SEQ ID NO 10
<211> LENGTH: 19
<212> TYPE: DNA
<213> ORGANISM: Homo sapiens

<400> SEQUENCE: 10
gcctcctgca ggctagaga                                                  19

<210> SEQ ID NO 11
<211> LENGTH: 20
<212> TYPE: DNA
<213> ORGANISM: Homo sapiens

<400> SEQUENCE: 11
gatgcacttt ttgcccttct                                                 20

<210> SEQ ID NO 12
<211> LENGTH: 19
<212> TYPE: DNA
<213> ORGANISM: Homo sapiens

<400> SEQUENCE: 12
gcaccaggtg gtctcctct                                                  19

<210> SEQ ID NO 13
<211> LENGTH: 20
<212> TYPE: DNA
<213> ORGANISM: Homo sapiens

<400> SEQUENCE: 13
tgacaaagtg gtcgttgagg                                                 20
```

PHARMACEUTICAL COMPOSITION AND METHOD FOR REDUCING SCAR FORMATION

BACKGROUND OF THE INVENTION

1. Field of the Invention

The present disclosure relates to pharmaceutical compositions and methods for reducing scar formation in a subject. More particularly, the disclosed invention relates to the use of a mixture of three nucleic acids for reducing scar formation.

2. Description of Related Art

Skin is the largest organ in human. It protects the internal organs/tissues from the environment. Vast numbers of people experience skin damages caused by trauma, burn or other external physical causes, as well as by diseases such as pressure, venous stasis and diabetes mellitus. The primary goals of the treatment of wounds include rapid wound closure and regeneration of functionally- and aesthetically-satisfactory skin tissues. However, wound healing is a dynamic, interactive process involving various factors, and despite the advances in cellular and molecular biology, the incidence of hypertrophic scarring remains high. These hypertrophic scars often lead to functional impairment and psychological morbidity, and may incur more healthcare expenses.

It has been observed that fetal wounds heal in a near perfect fashion without the formation of scars. The difference between fetal and adult cutaneous wound healing process has attracted much interest in the characterization of factors implicated in the scar formation process. Among various factors identified through this approach, transforming growth factor-beta (TGF-β) is believed to play a key role in the process of both wound healing and scar formation.

TGF-β is a type of cytokine that regulates cell growth, differentiation, apoptosis, fibrogenesis, and development in a wide range of biological systems. Typically, TGF-β is secreted in a latent form which is later activated through proteolytic activations mediated by TGF-β receptor type I (TGFBRI) and type II (TGFBRII). Human TGF-β has three isoforms, TGF-β1, TGF-β2 and TGF-β3; these isoforms have overlapping functions and predominantly mediate their effects through the intracellular SMAD pathway. In the cutaneous wound healing process, TGF-β1 is reported as being associated with immunosuppression, fibroblast migration and proliferation, wound contraction, granulation tissue formation, collagen synthesis and deposition, angiogenesis and re-epithelialization. Investigating the differential expressions of TGF-β isoforms in fetal and adult wounds found that the levels of TGF-β1 and TGF-β3 are respectively elevated in adult and fetal wounds, suggesting that TGF-β1 may be responsible for the scar formation in adult wounds whilst the scarless wound healing in fetal wounds may be due to increased level of TGF-β3.

Researchers have attempted to down-regulate the level of TGF-β1 at the wound site, using anti-TGF-β1 antibody or siRNA targeting TGF-β1, in hopes of achieving scarless wound healing. However, the TGF-β/SMAD signaling pathway involves dozens of mediators, and wound healing is a multi-stage process that requires different mediators in different stages. Accordingly, simply reducing the level of TGF-β1 does not yield satisfactory results. For example, full-thickness wounds in TGF-β1-deficient mice heal normally in the early stage; however, the TGF-β1 deficiency leads to inflammation that interferes with later stages of wound healing in these mice. Further, in TGF-β1 knockout mice lacking T and B cells (Tgfb1−/− Scid−/− mice), wound healing is delayed by approximately 1 week, as compared with immuno-deficient (Scid−/−) mice that have the wild-type Tgfb1 allele (Crowe M et al., J. Invest. Dermatol, 2000, 115, 3-11).

In view of the foregoing, there exists a need in the art for providing an effective treatment for reducing scar formation.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a pharmaceutical composition for reducing scar formation in a subject in need thereof. The pharmaceutical composition comprises a mixture of three nucleic acids targeting the human TGF-β receptor type I (TGFBRI) gene.

According to various embodiments of the present disclosure, the pharmaceutical composition comprises effective amounts of a first, second, and third nucleic acids and a pharmaceutically acceptable carrier. The three nucleic acids can be ribonucleic acids (RNAs) or deoxyribonucleic acids (DNAs). In the case where the three nucleic acids are RNAs, the sequences of said three nucleic acids respectively comprise the sequences of SEQ ID No: 1, SEQ ID No: 2 and SEQ ID No: 3. In the case where the three nucleic acids are DNAs, the sequences of said three nucleic acids respectively comprise the DNA sequences corresponding to that of SEQ ID No: 1, SEQ ID No: 2 and SEQ ID No: 3.

In certain embodiments of the present disclosure, the pharmaceutical composition further comprises a transfection-effective amount of a transfection reagent. Examples of the transfection reagent include cationic lipids and cell-penetrating peptides.

According to some embodiments, at least one of the first nucleic acid, the second nucleic acid, and the third nucleic acid is constructed into a virus vector. For example, the virus vector can be an Adeno-associated virus vector or a lentivirus vector. In various embodiments, the three nucleic acids can be respectively constructed into three separate virus vectors; alternatively, they can be constructed into a same virus vector; still alternatively, two of the three nucleic acids can be constructed into a same virus vector while the other nucleic acid is constructed into a different virus vector.

According to various embodiments of the present disclosure, the first nucleic acid, the second nucleic acid, and the third nucleic acid can be small interference ribonucleic acids (siRNAs), small hairpin ribonucleic acids (shRNAs), or micro-ribonucleic acids (miRNAs).

In certain embodiments of the present disclosure, the first nucleic acid, the second nucleic acid, and the third nucleic acid are siRNAs, wherein the sequences of the sense strand of the first, second and third nucleic acids are respectively identical to the sequences of SEQ ID No: 1, SEQ ID No: 2 and SEQ ID No: 3.

In another aspect, the present disclosure is directed to a method for reducing scar formation in a subject in need thereof. The method uses a mixture of three nucleic acids targeting the TGFBRI gene.

According to certain embodiments of the present disclosure, the method comprises the step of, administering to the subject, effective amounts of a first, second, and third nucleic acids. The sequences of said three nucleic acids respectively comprise the sequences of SEQ ID No: 1, SEQ ID No: 2 and SEQ ID No: 3 or the DNA sequences corresponding thereto.

In some optional embodiments of the present disclosure, the method further comprises the step of administering to the subject a transfection-effective amount of a transfection reagent. In various embodiments, the administration of the siRNA mixture is carried out prior to, concurrently with, or after the administration of the transfection reagent.

According to various embodiments, the transfection reagent and the siRNA mixture can be formulated in a single formulation or separate formulations.

According to various embodiments of the present disclosure, the transfection reagent can be one or more cationic lipids, polymer or cell-penetrating peptides.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which this invention belongs.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art.

Unless specified otherwise, in the polynucleotide notation used herein, the left-hand end is the 5'-end and the right-hand end is the 3'-end, in accordance with standard usage.

As used herein, the term "reduce" or "reducing" with respective to scar formation relates to measures that result in a lower incidence of scar formation, in a reduced degree of scar scale assesses by any available or future assessment methodology, or in a lower degree of scar area or scar volume, compared to the normal situation in which the scar formation is/has not interfered by man.

The term "effective amount" as used herein refers to the quantity of a component which is sufficient to yield a desired response. The specific effective amount will vary with such factors as the particular condition being treated, the physical condition of the subject (e.g., the subject's body mass, age, or gender), the type of mammal or animal being treated, the duration of the treatment, the nature of concurrent therapy (if any), and the specific formulations employed. An effective amount is also one in which any toxic or detrimental effects of the component or composition are outweighed by the therapeutically beneficial effects. Effective amount may be expressed, for example, in grams, milligrams or micrograms or as milligrams per kilogram of body weight (mg/kg). Alternatively, the effective amount can be expressed in the concentration of the active component in the pharmaceutical composition, such as molar concentration, mass concentration, volume concentration, molality, mole fraction, mass fraction and mixing ratio.

Specifically, the term "effective amount" used in connection with the nucleic acid described herein refers to the quantity of the nucleic acid which is sufficient to elicit the reduction of scar formation in the subject. Similarly, a "transfection-effective amount" is the quantity of the transfection reagent that is sufficient to result in the effective transfection of the nucleic acids.

As used herein, a "pharmaceutically acceptable carrier" is one that is suitable for use with humans and/or animals without undue adverse side effects (such as toxicity, irritation, and allergic response) commensurate with a reasonable benefit/risk ratio. Also, each carrier must be "acceptable" in the sense of being compatible with the other ingredients of the pharmaceutical formulation. The carrier can be in the form of a solid, semi-solid, or liquid diluent, cream or a capsule.

The term "carrier" as used herein means any inert substance (such as a powder or liquid) that forms a vehicle/excipient for the nucleic acids of the present disclosure. The carrier may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

The terms "application" or "administration" are used interchangeably herein to refer means providing the present nucleic acids or a pharmaceutical composition comprising the same to a subject to reduce or ameliorate scarring. According to various embodiments of the present disclosure, topical administration, local injection and transdermal delivery are common delivery routes. For example, the nucleic acids or pharmaceutical composition of the present invention is topically applied to the skin of the subject such that the nucleic acids or the present pharmaceutical composition reaches the target site (e.g., dermis) so as to reduce or ameliorate scar formation.

The term "subject" refers to a mammal including the human species that is treatable with the nucleic acids, pharmaceutical compositions, and/or methods of the present invention. The term "subject" is intended to refer to both the male and female gender unless one gender is specifically indicated.

The present invention is based, at least, on the finding that a mixture of three siRNAs targeting different regions of the human TGFBRI gene (NM_004612.2) is capable of reducing scar formation during the wound healing process. In particular, the combination of the three siRNAs magnifies the scar reduction effect of one of the siRNAs. Therefore, in one aspect, the present disclosure is directed to a mixture comprising said three siRNAs. Moreover, the siRNA mixture according to the present disclosure can be provided for use in reducing (including preventing) scar formation; for example, it shall be manufactured as a medicament, e.g., comprised in a pharmaceutical composition. The present siRNA mixture and the pharmaceutical composition comprising the same can also be applied in a method for reducing scar formation. Accordingly, the present disclosure also contemplates a method for reducing scar formation in a subject in need thereof.

According to certain embodiments of the present disclosure, the three siRNAs respectively have a sense strand having the nucleotide sequence of SEQ ID No: 1, SEQ ID No: 2 and SEQ ID No: 3. siRNAs are often double stranded with blunt, 3'-overhang or 5'-overhang ends. In the working examples provided hereinbelow, the siRNAs are blunt-ended, and the anti-sense strands of the siRNAs are perfect complements of the respective sense strands.

As could be appreciated by persons having ordinary skill in the art, the silencing or inhibition of mRNA translation can be achieved by nucleotide molecules other than siRNAs, and these nucleotide molecules are also contemplated by embodiments of the present invention. For instance, shRNA is an RNA molecule that contains sense and anti-sense sequences connected by a short spacer of nucleotides that enables the molecule to form a loop structure, and according to embodiments of the present disclosure, the first, second and third nucleic acids can be shRNAs in which the sense sequences of the shRNAs are respectively identical to the sequences of SEQ ID No: 1, SEQ ID No: 2 and SEQ ID No: 3. In other embodiments, the nucleic acids are provided in the form of a miRNA or a precursor (e.g., pri-miRNAs or pre-miRNAs) thereof, and the miRNAs or the precursors respectively have a sequence comprising the sequences of SEQ ID No: 1, SEQ ID No: 2 and SEQ ID No: 3. Still alternatively, the present nucleic acids can be any double- or single-stranded antisense oligonucleotides comprising the sequences of SEQ ID Nos: 1-3 (or the DNA sequences corresponding thereto).

In certain embodiments, the pharmaceutical composition may further comprise a transfection reagent in an amount sufficient to facilitate or enable the transfection of the siRNAs into the target (or host) cells. As could be appreciated, the transfection reagent and the siRNA mixture can be formulated into a single formulation or in separate formulations. Alternatively or additionally, the target cells can be treated by one or more external stimuli, such as electroporation or calcium phosphate to enhance the transfection efficacy.

According to certain embodiments of the present disclosure, the transfection reagent can be cationic lipids. Commercially available cationic lipids include, but are not limited to, Oligofectamine™, LipofectArnine™, LipofectAmine 2000™ (Invitrogen). In some embodiments, the transfection reagent can be cell-penetrating peptides, such as PepMute™ (SignaGen), N-TER™ Nanoparticle (Sigma-Aldrich), and DeliverX™ (Isogen).

The pharmaceutical compositions containing the siRNAs may include additional components that protect the stability of the siRNA, prolong the lifetime of the siRNA, potentiate the function of the siRNA, or target the siRNA to specific tissues/cells.

In optional embodiments, the three nucleic acids comprised in the present pharmaceutical composition may be constructed into one or more virus vectors; such as Adeno-associated virus vectors or lentivirus vectors. In various embodiments, one virus vector may carry all three nucleic acids; alternatively, there can be more than one virus vectors respectively carrying one or two of said three nucleic acids.

According to various embodiments of the present disclosure, the present siRNA mixture (or, shRNA mixture, miRNA mixture, or one or more virus vectors described above; similarly hereinafter) or the pharmaceutical composition comprising the same can be administered to the subject; in particular, the target site of the subject, so as to ameliorate scar formation during the wound healing process. For example, the siRNA mixture or the pharmaceutical composition can be topically applied to the wound site of the subject. Alternatively, the siRNA mixture or the pharmaceutical composition is formulated as a transdermal dosage form which, after being applied to the epidermis of the subject reaches the wound site located at the dermal layer. Still alternatively, the siRNA mixture or the pharmaceutical composition is locally injected to wound site. In addition to local delivery, the siRNA mixture or the pharmaceutical composition may also be administered systemically, such as intravenously, and migrate to the site of the traumatized tissue. In these cases, the pharmaceutical composition may optionally comprise one or more carriers to improve the local or systemic delivery of the siRNA mixture.

According to optional embodiments of the present disclosure, the method for reducing scar formation further comprises the step of administering to the subject a transfection-effective amount of a transfection reagent. In various embodiments, the administration of the siRNA mixture is carried out prior to, concurrently with, or after the administration of the transfection reagent. In the case where the administration of the siRNA mixture occurs concurrently with the administration of the transfection reagent, the siRNA mixture and the transfection reagent can be formulated in the same formulation or separate formulations.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Culture of Human Hypertrophic Scar Fibroblasts.

Primary cultured human hypertrophic scar fibroblasts (hHSF) were established from 5 skin samples (4 males and 1 female, ages 36-86). All of these skin samples were discard scar tissues from scar revision surgery. The sample collection protocol was approved by the Institutional Review Board of Tri-Service General Hospital (Taipei, Taiwan, R.O.C.), and written informed consent was obtained from each donor. Specimens were processed as follows. Briefly, the specimen was trimmed into small pieces, and digested in 0.2% Dispase II (Roche Applied Science, Mannheim, Germany) and in Leibovitz's L-15 medium (Gibco, Grand Island, N.Y.) to remove the epithelium. The dermis layer was then incubated in 0.05% collagenase in Dulbecco's modified Eagle's medium (DMEM) (Gibco) supplemented with 10% fetal bovine serum (FBS) (Gibco) at 37° C., 5% $CO_2$ for 24 hours. The resulting cells were then maintained in DMEM supplemented with 10% FBS. The medium was refreshed every 2-3 days. Fibroblasts between passages three to six were harvested for subsequent studies.

siRNA Transfection.

The design of TGFBRI Stealth siRNA was based on the program BLOCK-IT™ RNAi Designer (Invitrogen, Carlsbad, Calif.) and NCBI-BLAST. Three selected siRNA duplexes (siTGBRI-a: GACAUCUAUGCAAUGGGC-UUAGUAU (SEQ ID No: 1); siTGBRI-b: GCAUCUCA-CUCAUGUUGAUGGUCUA (SEQ ID No: 2); and siTG-BRI-c: AGUAAGACAUGAUUCAGCCACAGAU (SEQ ID No: 3)) cover different regions of the sense strand of human TGFBRI mRNA (NM_004612.2). These three siRNA duplexes were also designed to match rabbit TGF-BRI mRNA (XM_002708153.1). The designed TGFBRI siRNA sequences were custom synthesized by Invitrogen. A nonspecific scrambled siRNA (5'-UUCUCCGAACGUGU-CACGUTT-3') (MDbio, Taipei, Taiwan) was used as a control. The three TGFBRI siRNAs, alone or in combination, and scrambled siRNA were each reverse transfected into fibroblasts with the PepMute transfection kit (Signa-Gen, Rockville, Md.). Briefly, TGFBRI siRNA mixture or single TGFBRI siRNA was diluted in 100 µl transfection buffer, then 1 µl of PepMute reagent was added, and the mixture was incubated at room temperature for 15 minutes. Cells were suspended in 900 µl of DMEM with 10% FBS, and then planted in 6 well culture dishes ($2\times10^5$ cells/well) with 100 µl diluted siRNA duplexes and incubated at 37° C., 5% $CO_2$. The final siRNA concentration was 60 nM, depending on the optimal test. After 24 hours, the medium was replaced with DMEM, 5% FBS with or without additional TGF-β1 2 ng/ml (Invitrogen). Five hHSF strains were treated using the same process.

RNA Isolation, Reverse Transcription, and Quantitative Real-Time PCR.

Gene expression of treated cells was analyzed at 72 hours after siRNA transfection. Total RNA was isolated using the RNeasy Mini kit (Qiagen GmbH, Hilden, Germany). RNA quality and quantity were determined with NanoDrop2000 (Thermo Fisher Scientific, Wilmington, Del.). RNA was then converted to cDNA with the MultiScript High Capacity cDNA Reverse Transcription Kit (Applied Biosystems, Foster City, Calif.). Gene expression levels were measured for TGFBRI and glyceraldehyde 3-phosphate dehydrogenase (GAPDH) by quantitative real-time PCR using QuantiFast® Probe Assay kit (Qiagen). For Type I collagen, Type III collagen, connective tissue growth factor (CTGF), and fibronectin, gene expression levels were quantified by using appropriate primers (Table 1) with Power SYBR Green PCR master mix (Invitrogen), and GAPDH gene expression served as an internal control. TaqMan real-time PCR and SYBR Green quantitative real-time PCR were performed and analyzed in the LightCycler 480 System (Roche Applied Science).

TABLE 1

| Gene | Sequences (5' to 3') | SEQ ID NO. |
|---|---|---|
| Human Type I collagen a2 | Forward-TGCTGCTGGTCAACCTGGTGC | 4 |
|  | Reverse-ACTTCCAGCAGGACCGGGGG | 5 |
| Human Type III collagen a1 | Forward-CTGGTGGTAAAGGCGAAATG | 6 |
|  | Reverse-CCAGGAGCACCATTAGCAC | 7 |

TABLE 1-continued

| Gene | Sequences (5' to 3') | SEQ ID NO. |
|---|---|---|
| Human Fibronectin | Forward-ACAACACCGAGGTGACTGAGAC | 8 |
| | Reverse-GGACACAACGATGCTTCCTGAG | 9 |
| Human CTGF | Forward-GCCTCCTGCAGGCTAGAGA | 10 |
| | Reverse-GATGCACTTTTTGCCCTTCT | 11 |
| Human GAPDH | Forward-GCACCAGGTGGTCTCCTCT | 12 |
| | Reverse-TGACAAAGTGGTCGTTGAGG | 13 |

Western Blotting of TGFBRI Protein Expression.

TGFBRI protein expression of treated cells was analyzed by western blotting at day 5 after TGFBRI siRNA transfection. Cells were lysed in Pro-Prep protein extraction solution (Intron, Seoul, Korea) with protease inhibitors (Roche Applied Science). Protein extracts were applied to a 4-20% gradient gel (Bio-Rad, Hercules, Calif.) and then transferred to PVDF membranes. PVDF membranes were immunoblotted with rabbit anti human TGFBRI antibody (GeneTex, San Antonio, Tex.), with mouse anti GAPDH (GeneTex, San Antonio, Tex.) as the internal control. Appropriate secondary antibody conjugated with HRP was incubated with membrane to activate chemiluminescent substrate (Visual protein, Taipei, Taiwan). Protein expression levels were detected and quantitated by UVP BioImaging System (UVP, Upland, Calif.).

Fibroblast Proliferation Assay.

Fibroblast proliferation was quantified using Cell Counting Kit-8 (Boster Biological Technology, Wuhan, China). In brief, hHSF derived from 5 skin samples were seeded at $5 \times 10^3$ cells/well in triplicate in 96-well plate and treated with TGFBRI siRNAs 60 nM, as described above. One day after treatment, the medium was changed to culture medium with or without the addition of TGF-β1 2 ng/ml. The medium was refreshed every 2 days. At 3, 7, and 10 days after treatment, 10 μl CCK-8 solution in 90 μl DMEM without phenol red was added into each well. After 1 hour incubation, absorbance was recorded at 450 nm.

Enzyme-Linked Immunosorbent Assay of Type I Collagen.

For determining type I collagen production in the supernatant fluid of fibroblasts after TGFBRI siRNA transfection, the siRNA-transfected fibroblasts were incubated in culture medium with additional TGF-β1 2 ng/ml at 37° C., 5% $CO_2$. The medium was refreshed every other day. At day 7, the medium was collected and the supernatants were measured by enzyme-linked immunosorbent assay (ELISA) using the human collagen Type I ELISA kit (BlueGene, Shanghai, China). Absorbance was recorded at 450 nm against standard curve by spectrophotometer (Bio-Rad). All measurements were done in triplicate, performed in 5 hHSF strains, and expressed in μg/mL.

Animal Model.

Adult New Zealand white rabbits, which had been raised in the animal care center at the National Defense Medical Center, were purchased from the Animal Health Research Institute (New Taipei City, Taiwan). All surgical approaches and procedures were approved by the Institutional Animal Care and Use Committee of the National Defense Medical Center. Six-month-old rabbits (3-3.5 kg) were sedated with an intramuscular injection of zoletil (1 mg/kg) plus xylazine (3 mg/kg) and anesthetized by inhalation using isoflurane 1.5-4%. Ketoprofen (10 mg/kg) was applied as an analgesic during the experiment. Four 1.8×1.8 $cm^2$ full thickness skin-defect wounds with removal of the perichondrium were shaped on the concave side of each ear. The wounds were covered with Vaseline gauze and fixed with CoBan (3M Healthcare, St Paul, Minn.) for 2 weeks without dressing change unless a wound became infected. These procedures would form about 5 mm granulation tissue on the edges of the lesion side at day 14. Eighty-eight wounds were divided into TGFBRI siRNA-treatment and control groups. In the TGFBRI siRNA treatment group, the granulation sites of each wound was injected with 240 pmol of TGFBRI siRNAs in 40 μl transfection buffer prepared with 2.5 μl of PepMute reagent at 2, 3, and 4 weeks after wounding. Control groups were treated using the same procedures without siRNA injection. Before siRNA injection, animals were sedated as described above. The repaired wounds were evaluated by the Vancouver Scar Scale (VSS) (Fearmonti, R., Bond, J., Erdmann, D. & Levinson, H. (2010). A review of scar scales and scar measuring devices. *Eplasty* 10: e43.) at 6, 10, and 14 weeks after skin defect surgery. Animals were then sacrificed by overdose anesthetics to harvest scar specimens. Scar specimens were fixed with 10% formalin, embedded in paraffin, sectioned at 5 μm onto glass slides, and stained with Masson's trichrome stain (Sigma-Aldrich, St. Louis, Mo.). Hypertrophied dermis was evaluated using the scar elevation index (SEI) (Kloeters, O., Tandara, A. & Mustoe, T. A. (2007). Hypertrophic scar model in the rabbit ear: a reproducible model for studying scar tissue behavior with new observations on silicone gel sheeting for scar reduction. *Wound Repair Regen* 15 Suppl 1: S40-45.).

Statistical Analysis.

All data were expressed as means±standard deviation (SD). Statistical analyses were performed using one-way ANOVA. Unless specified otherwise, differences with a P-value less than 0.05 were considered to be statistically significant (P<0.05). *P<0.05; P<0.01; *P<0.001.

Example 1

TGBRI siRNA Mixture Reduces TGFBRI Gene Expression

In this example, human hypertrophic scar fibroblasts were transfected with either 60 nM of siTGBRI-a, siTGBRI-b, siTGBRI-c or scrambled siRNA or 60 nM of siTGBRI mixture containing siTGBRI-a, siTGBRI-b and siTGBRI-c. TGFBRI gene expression was confirmed by quantitative reverse transcription PCR analysis at day 3, according to the protocol set forth above. The original mRNA levels from cells transfected with scrambled siRNA 1 were normalized to 1, and the data provided in FIG. 1 are expressed as fold change between the control groups and each treatment group.

Figure 1:
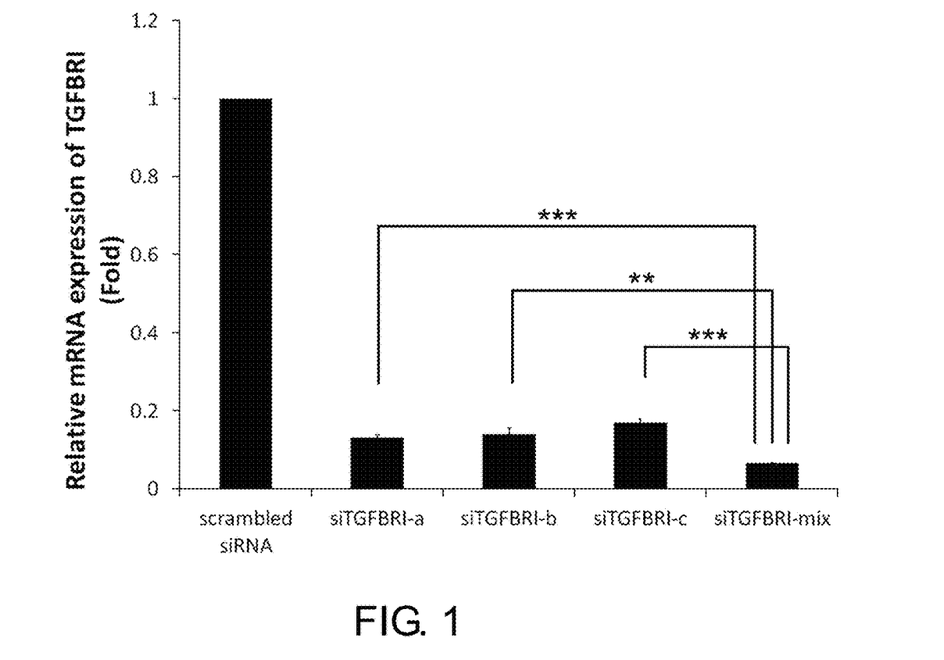
FIG. 1 is a bar graph illustrating the relative mRNA expression of TGFBRI gene in human hypertrophic scar fibroblasts at day 3 (n=3), according to Example 1 of the present disclosure.

As could be seen in FIG. 1, said three siRNAs, alone or in combination, significantly reduced the mRNA expression level of TGFBRI gene. However, the present inventor observed that the siRNA mixture (siTGBRI-mix) elicited a greater effect than that induced by any of the three siRNAs, in terms of the reduction of the mRNA expression of TGFBRI. In other words, the combination of three siRNAs achieved a synergistic effect. Further, statistical analysis revealed that the difference between the siTGFBRI-mix-treated group and any of the single siRNA-treated group is quite significant. Accordingly, this synergistic effect is greater than those which would have been expected from the prior art to an unobvious extent.

Figure 2:
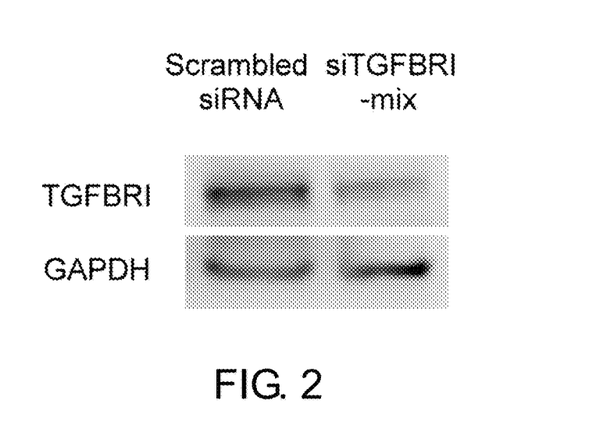
FIG. 2 is a representative photograph of the Western blot illustrating the protein expression of TGFBRI gene and GAPDH gene in human hypertrophic scar fibroblasts at day 5, according to Example 1 of the present disclosure.
Figure 3:
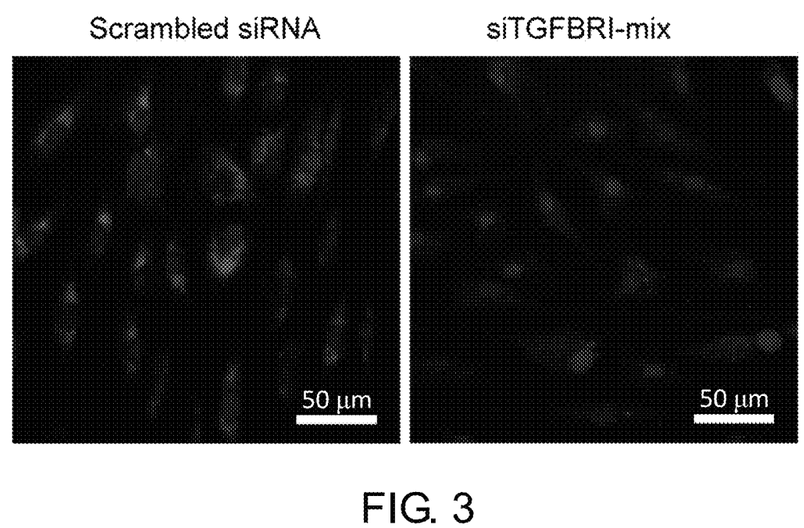
FIG. 3 provides representative immunofluorescence staining photographs for TGFBRI at 5 days after transfected with scrambled siRNA or siTGFBRI-mix, according to Example 1 of the present disclosure.

Western blot analysis (FIG. 2) and immunofluorescence staining (FIG. 3) also confirmed that siTGFBRI-mix reduced the expression level of TGFBRI protein.

Example 2

TGBRI siRNA Mixture Inhibit Cell Proliferation of Human Dermal Fibroblasts

Figure 4:
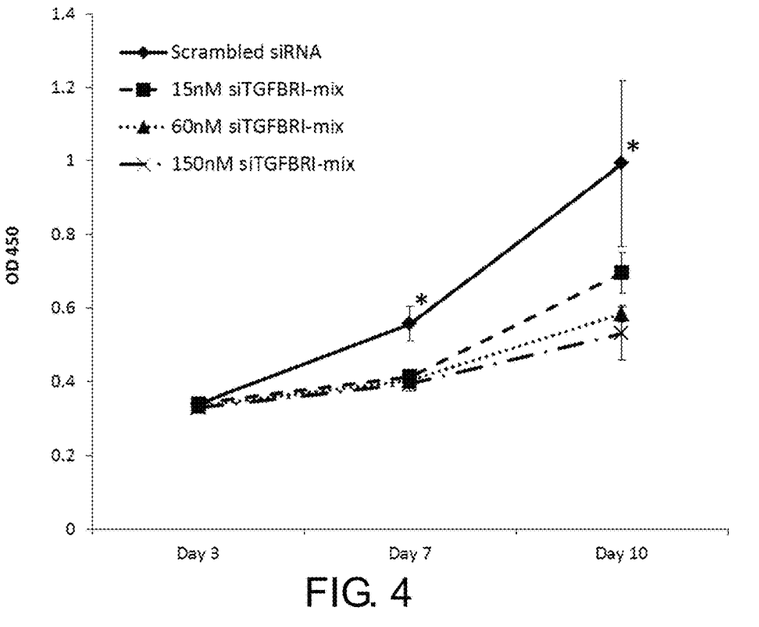
FIG. 4 is the growth curve of human hypertrophic scar fibroblasts at days 3, 7, and 10 after siRNA transfection with siTGFBRI-mix or scrambled siRNA (n=5), according to Example 2 of the present disclosure.

Cell proliferation of human hypertrophic scar fibroblasts transfected with siTGBRI-mix of various concentrations (15, 60 or 150 nM) or scrambled siRNA (60 nM) was investigated at days 3, 7, and 10 after siRNA transfection. The results, as illustrated in FIG. 4, indicate that the administration of 15-150 nM siTGBRI-mix effectively inhibits fibroblast proliferation. During the early stage (e.g., the first week) after transfection, the concentration of siTGBRI-mix did not significantly affect the inhibitory effect; however, at 10 days post-transfection, dose-dependent inhibitory effect was observed, in which a higher siTGBRI-mix concentration achieved a greater level of inhibition on fibroblast proliferation.

Figure 5:
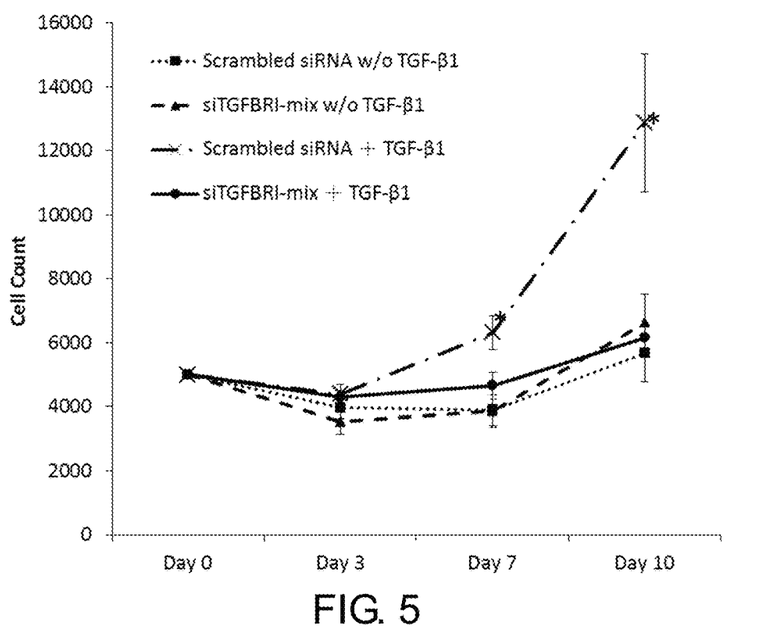
FIG. 5 is the growth curve of human hypertrophic scar fibroblasts at days 3, 7, and 10 after siRNA transfection with siTGFBRI-mix or scrambled siRNA, with or without TGF-βI stimulation (n=5), according to Example 2 of the present disclosure.

Additionally, the human hypertrophic scar fibroblasts were transfected with 60 nM siTGFBRI-mix or scrambled siRNA 60 nM, with or without the addition of TGF-$\beta$I (2 ng/ml). Cell counts obtained from each treatment group at 3, 7 and 10 days post-transfection are summarized in FIG. 5. By comparing the groups treated with "scrambled siRNA+TGF-$\beta$I" and "siTGFBRI-mix+TGF-$\beta$I", it is found that the administration of siTGFBRI-mix significantly inhibited the fibroblast proliferation.

Example 3

Downregulating TGFBRI Reduces ECM Production

The formation of extracellular matrix involves various mediators and components, such as type I collage, type III collagen, fibronectin and connective tissue growth factor (CTGF). In this example, the relative mRNA expression levels of the above-mentioned proteins in human hypertrophic scar fibroblasts transfected with 60 nM siTGFBRI-mix or scrambled siRNA, with or without the addition of TGF-$\beta$I were analyzed real-time PCR at 72 hours after siRNA transfection. The original mRNA levels from cells transfected with scrambled siRNA and stimulated with TGF-$\beta$1 (positive control) were normalized to 1, and the data provided in FIG. 6 are expressed as fold change of each treatment group with respect to the positive control.

Figure 6:
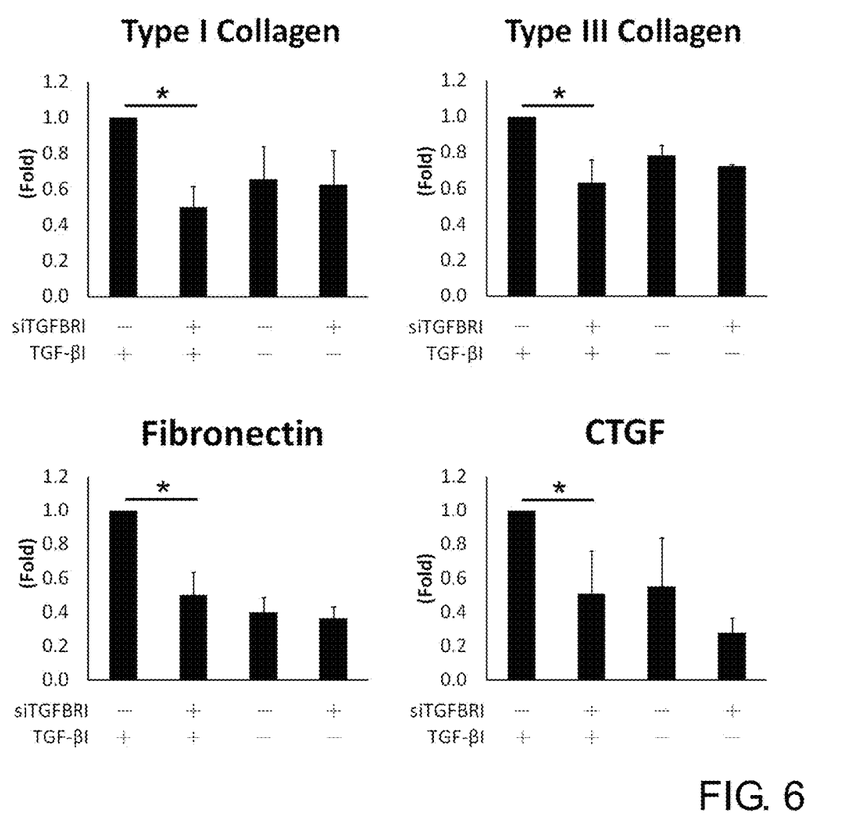
FIG. 6 provides bar graphs illustrating relative mRNA expression of various genes in human hypertrophic scar fibroblasts at day 3 (n=5), according to Example 3 of the present disclosure.

The data in FIG. 6 illustrates that in the group treated with "siTGFBRI-mix+TGF-$\beta$I," the mRNA expression levels of type I collage, type III collagen, fibronectin and CTGF were substantially reduced, as compared to the group treated with "scrambled siRNA+TGF-$\beta$I."

Figure 7:
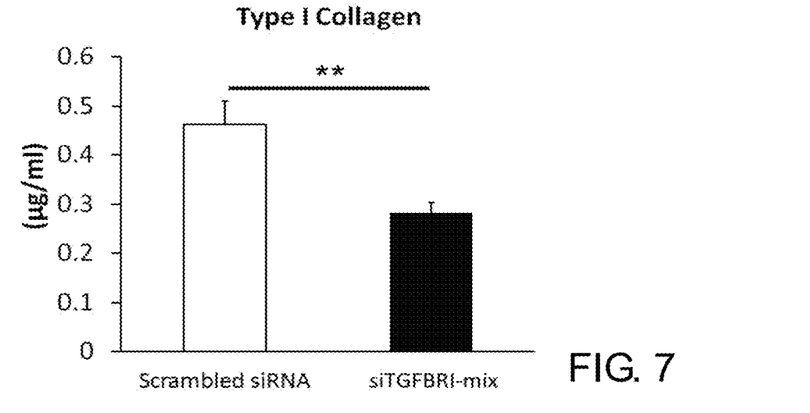
FIG. 7 is a bar graph illustrating the result of enzyme-linked immunosorbent assay for secreted Type I collagen at day 7 after transfection with scrambled siRNA or siTGF-BRI-mix (n=5), according to Example 3 of the present disclosure.

Medium of treated cells was collected at day 7 after siRNA transfection and analyzed by ELISA for secreted type I collagen. The results of ELISA, as summarized in FIG. 7, indicate that the transfection of siTGFBRI-mix substantially reduced the synthesis of type I collagen in fibroblasts.

Figure 8:
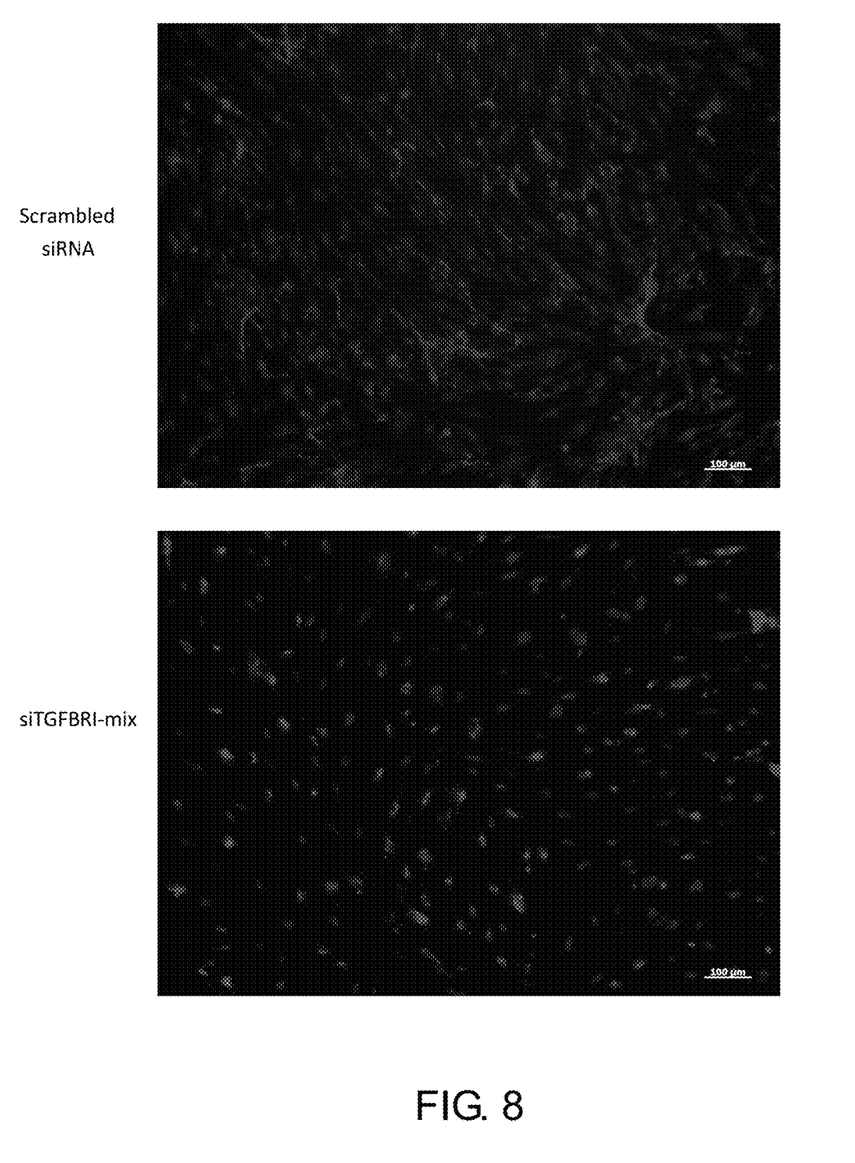
FIG. 8 provides representative immunofluorescence staining photographs for fibronectin at day 6 after transfection with scrambled siRNA or siTGFBRI-mix, according to Example 3 of the present disclosure.

FIG. 8 is a photograph of immunofluorescence staining for fibronectin. As could be seen in FIG. 8, the transfection with siTGFBRI-mix resulted in a reduction of fibronectin in ECM at 6 days after transfection.

In view of the foregoing, the administration of siTGFBRI-mix reduced the ECM production in the transfected fibroblasts.

Example 4

TGFBRI siRNA Mixture Attenuate Hypertrophic Scarring In Vivo siTGFBRI-mix was injected into the wound granulation tissue on the rabbit ear at 2, 3, and 4 weeks after wounding. The repaired tissues were imaged at 6, 10, and 14 weeks after wounding.

Figure 9:
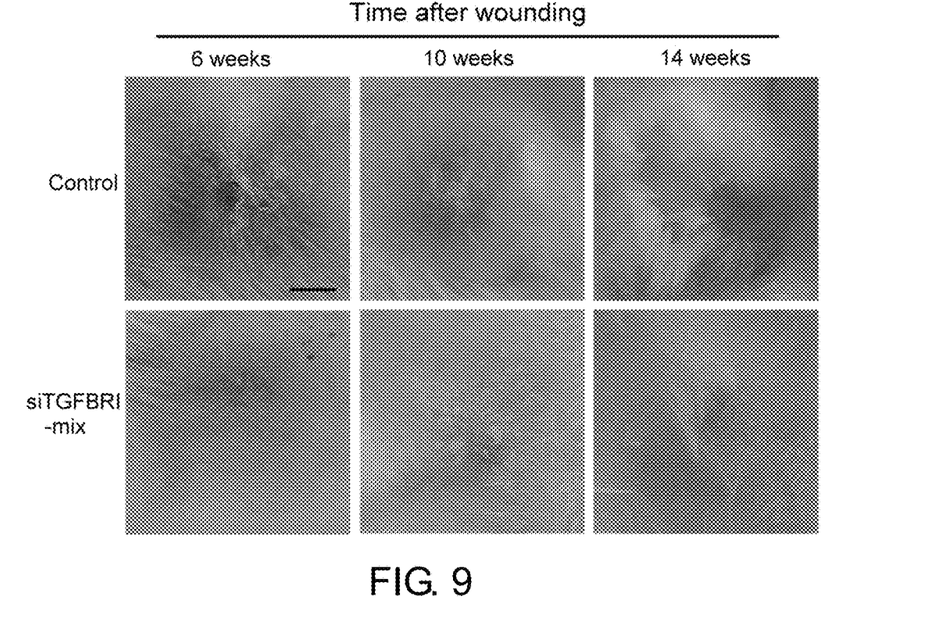
FIG. 9 provide representative photographs of the wound granulation tissue on the rabbit ear at 6, 10, and 14 weeks after wounding, according to Example 4 of the present disclosure; bar=500 μm.

In FIG. 9, the wounds in rabbits treated with siTGFBRI-mix healed, as compared to wounds in control rabbits. Specifically, the scar area and scar volume in siTGFBRI-mix-treated rabbits were smaller than that in control rabbits. Also, judging from the paler color in the scar of siTGFBRI-mix-treated rabbits, there is less pigmentation in the siTGFBRI-mix-treated wounds.

Figure 10:
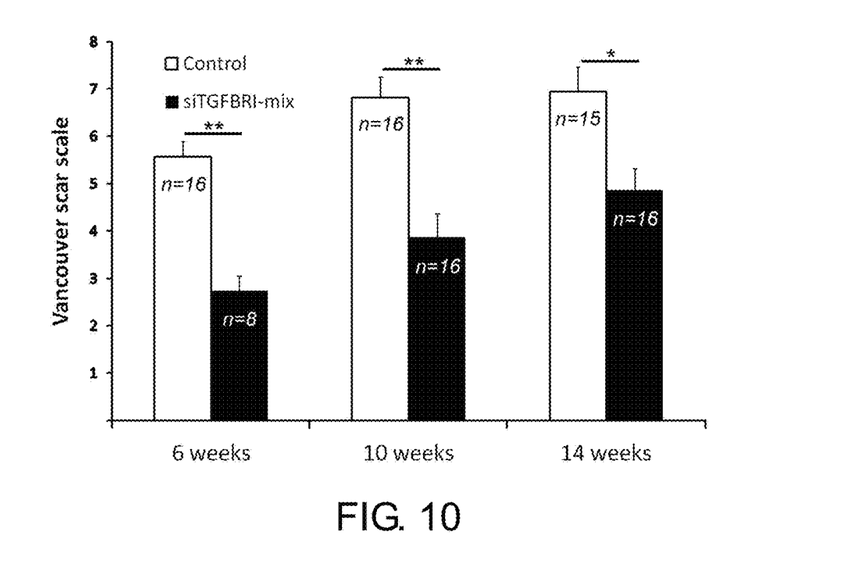
FIG. 10 is a bar graph summarizing the Vancouver scar scale of the wounds on the rabbit ear at 6, 10, and 14 weeks after wounding, according to Example 4 of the present disclosure.

Repaired wounds were evaluated by the Vancouver scar scale (VSS), and the results are summarized in FIG. 10. VSS assesses the vascularity, height/thickness, pliability, and pigmentation of the repaired tissue, and is widely applicable to evaluate therapy and as a measure of outcome in burn studies. According to VSS assessment, a scale of zero means a perfectly or near perfectly healed tissue. The data in FIG. 10 confirms that the treatment of siTGFBRI-mix effectively ameliorated the formation of hypertrophic scar in vivo.

Example 5

TGFBRI siRNA Mixture Reduces Collagen Deposition In Vivo

Scar tissues of rabbits treated in Example 4, above, were harvested at 6, 10, and 14 weeks after wounding, and sections were prepared as described in "Materials and Methods" section, above.

Figure 11:
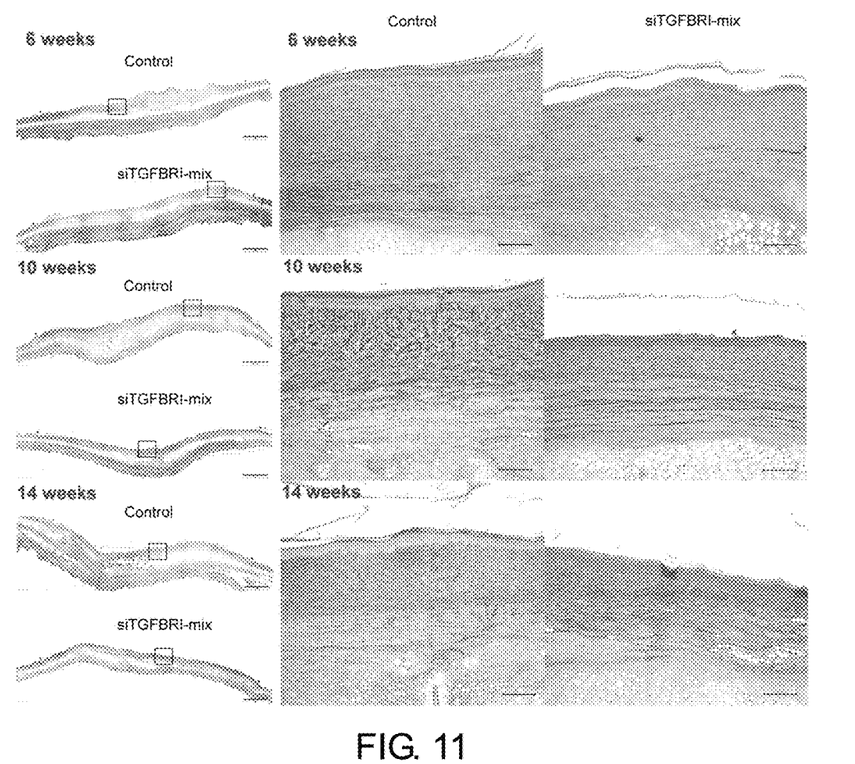
FIG. 11 provides representative photographs of the skin sections of Scar tissues were harvested at 6, 10, and 14 weeks after wounding (left panel; bar=2 mm), the partial enlargement view of the skin sections are provided in the middle and right panels (bar=100 μm), according to Example 5 of the present disclosure.

Representative photomicrographs of repaired tissues are provided in FIG. 11. As can be seen in FIG. 11, the application of siTGFBRI-mix significantly reduced collagen deposition in the repaired tissue for the collagen (blue) is less dense in the siTGFBRI-mix-treated group.

Figure 12:
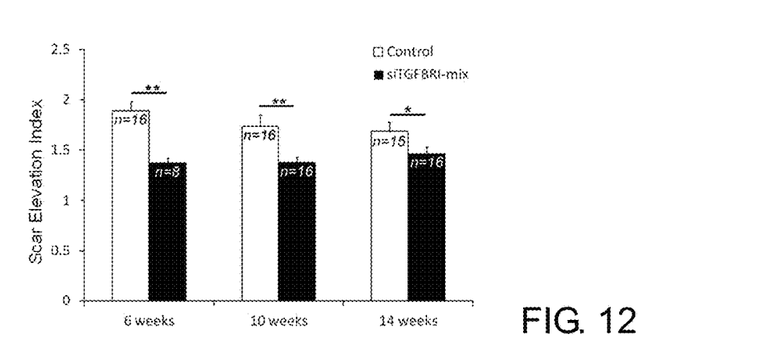
FIG. 12 is a bar graph summarizing the scar elevation index of the wounds on the rabbit ear at 6, 10, and 14 weeks after wounding, according to Example 5 of the present disclosure.

The tissue sections were further evaluated by the scar elevation index (SEI). SEI is a histologic measure of the height of the scar compared with the normal scar. The degree of hypertrophy of each scar is the ratio of tissue height of the total wound area to the area of normal tissue below the hypertrophic scar, with an SEI of 1 suggesting no raised height of the scar. The SEI results summarized in FIG. 12 indicates that less scar elevation was observed in rabbits treated with siTGFBRI-mix, as compared with that of the control rabbit.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A pharmaceutical composition for reducing scar formation, comprising,
   an effective amount of a first nucleic acid or a first expression vector expressing the first nucleic acid, wherein the sequence of the first nucleic acid comprises the sequence of SEQ ID No: 1;
   an effective amount of a second nucleic acid or a second expression vector expressing the second nucleic acid, wherein the sequence of the second nucleic acid comprises the sequence of SEQ ID No: 2;
   an effective amount of a third nucleic acid or a third expression vector expressing the third nucleic acid, wherein the sequence of the third nucleic acid comprises the sequence of SEQ ID No: 3; and
   a pharmaceutically acceptable carrier;
   wherein the first nucleic acid, the second nucleic acid, and the third nucleic acid are small interference ribonucleic acids (siRNAs), or small hairpin ribonucleic acids (shRNAs).

2. The pharmaceutical composition of claim 1, further comprising a transfection-effective amount of a transfection reagent.

3. The pharmaceutical composition of claim 2, wherein the transfection reagent is a cationic lipid or a cell-penetrating peptide.

4. The pharmaceutical composition of claim 3, wherein the transfection reagent comprises one or more cell-penetrating peptides.

5. The pharmaceutical composition of claim 1, wherein at least one of the first nucleic acid, the second nucleic acid, and the third nucleic acid is constructed into a virus vector.

6. The pharmaceutical composition of claim 5, wherein the virus vector is an Adeno-associated virus vector or a lentivirus vector.

7. The pharmaceutical composition of claim 5, wherein the first nucleic acid, the second nucleic acid, and the third nucleic acid are respectively constructed into three virus vectors.

8. The pharmaceutical composition of claim 1, wherein the first nucleic acid, the second nucleic acid, and the third nucleic acid are siRNAs.

9. A method for reducing scar formation in a subject in need thereof, comprising the step of,
   administering to the subject, an effective amount of a first nucleic acid or a first expression vector expressing the first nucleic acid, wherein the sequence of the first nucleic acid comprises the sequence of SEQ ID No: 1; an effective amount of a second nucleic acid or a second expression vector expressing the second nucleic acid, wherein the sequence of the second nucleic acid comprises the sequence of SEQ ID No: 2; and an effective amount of a third nucleic acid or a third expression vector expressing the third nucleic acid, wherein the sequence of the third nucleic acid comprises the sequence of SEQ ID No: 3;
   wherein the first nucleic acid, the second nucleic acid, and the third nucleic acid are small interference ribonucleic acids (siRNAs), or small hairpin ribonucleic acids (shRNAs).

10. The method of claim 9, further comprising the step of administering to the subject a transfection-effective amount of a transfection reagent.

11. The method of claim 10, wherein the transfection reagent is administered to the subject prior to or after the administration of the first nucleic acid, the second nucleic acid, and the third nucleic acid.

12. The method of claim 10, wherein the transfection reagent is administered to the subject concurrently with the administration of the first nucleic acid, the second nucleic acid, and the third nucleic acid.

13. The method of claim 10, wherein the transfection reagent is a cationic lipid or a cell-penetrating peptide.

14. The method of claim 10, wherein the transfection reagent comprises one or more cell-penetrating peptides.

15. The method of claim 9, wherein at least one of the first nucleic acid, the second nucleic acid, and the third nucleic acid is constructed into a virus vector.

16. The method of claim 15, wherein the virus vector is an Adeno-associated virus vector or a lentivirus vector.

17. The method of claim 15, wherein the first nucleic acid, the second nucleic acid, and the third nucleic acid are respectively constructed into three virus vectors.

18. The method of claim 9, wherein the first nucleic acid, the second nucleic acid, and the third nucleic acid are siRNAs.

* * * * *